US009801566B2

(12) United States Patent
Verard et al.

(10) Patent No.: US 9,801,566 B2
(45) Date of Patent: Oct. 31, 2017

(54) AUTOMATIC IDENTIFICATION OF INSTRUMENTS USED WITH A SURGICAL NAVIGATION SYSTEM

(71) Applicant: Medtronic Navigation, Inc., Louisville, CO (US)

(72) Inventors: Laurent Verard, Eindhoven (NL); Robert Teichman, Lafayette, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 14/087,735

(22) Filed: Nov. 22, 2013

(65) Prior Publication Data

US 2014/0081128 A1    Mar. 20, 2014

Related U.S. Application Data

(62) Division of application No. 11/708,157, filed on Feb. 19, 2007, now Pat. No. 8,600,478.

(51) Int. Cl.
| | |
|---|---|
| *A61B 5/05* | (2006.01) |
| *A61B 5/06* | (2006.01) |
| *A61B 90/00* | (2016.01) |
| *A61B 34/20* | (2016.01) |
| *A61B 90/90* | (2016.01) |

(Continued)

(52) U.S. Cl.
CPC ............... *A61B 5/06* (2013.01); *A61B 34/20* (2016.02); *A61B 90/36* (2016.02); *A61B 90/90* (2016.02); *A61B 90/98* (2016.02); *A61B 2034/102* (2016.02); *A61B 2034/105* (2016.02); *A61B 2034/107* (2016.02); *A61B 2034/2051* (2016.02); *A61B 2034/256* (2016.02); *A61B 2090/365* (2016.02); *A61B 2090/376* (2016.02)

(58) Field of Classification Search
CPC ..... A61B 19/44; A61B 19/52; A61B 19/5244; A61B 2019/448; A61B 2019/502
See application file for complete search history.

(56) References Cited

U.S. PATENT DOCUMENTS

| | | | |
|---|---|---|---|
| 4,705,038 | A | 11/1987 | Sjostrom et al. |
| 5,442,082 | A | 8/1995 | Uphues et al. |

(Continued)

FOREIGN PATENT DOCUMENTS

| | | |
|---|---|---|
| DE | 10239710 | 3/2004 |
| EP | 1518508 | 3/2005 |

(Continued)

OTHER PUBLICATIONS

"Chips are just what the doctor ordered", article dated Nov. 14, 2006, The Sydney Morning Herald, http://www.smh.com.au/articles/2006/11/13/1163266481840.html?page=fullpage, printed Dec. 11, 2006 (2 pgs).

(Continued)

*Primary Examiner* — James Kish
(74) *Attorney, Agent, or Firm* — Harness Dickey

(57) ABSTRACT

A system and apparatus taught to determine the identification and selected information relating to surgical instruments near a reader. The information can be stored on a member operable to transmit the information to a reader at a selected time. The information can be used in a navigation system to assist in navigation of the instrument relative to a patient.

20 Claims, 4 Drawing Sheets

(51) Int. Cl.
*A61B 90/98* (2016.01)
*A61B 34/10* (2016.01)
*A61B 34/00* (2016.01)

(56) References Cited

U.S. PATENT DOCUMENTS

| | | |
|---|---|---|
| 5,610,811 A | 3/1997 | Honda et al. |
| 5,740,808 A | 4/1998 | Panescu et al. |
| 5,923,001 A | 7/1999 | Morris et al. |
| 5,931,824 A | 8/1999 | Stewart et al. |
| 6,068,627 A | 5/2000 | Orszulak et al. |
| 6,226,548 B1 | 5/2001 | Foley et al. |
| 6,264,647 B1 | 7/2001 | Lechot et al. |
| 6,366,206 B1 | 4/2002 | Ishikawa et al. |
| 6,381,485 B1 | 4/2002 | Hunter et al. |
| 6,402,743 B1 | 6/2002 | Orszulak et al. |
| 6,434,507 B1* | 8/2002 | Clayton ............ A61B 17/32002 600/104 |
| 6,529,006 B1 | 3/2003 | Hayes |
| 6,540,739 B2 | 4/2003 | Lechot et al. |
| 6,685,701 B2 | 2/2004 | Orszulak et al. |
| 6,689,138 B2 | 2/2004 | Lechot et al. |
| 6,861,954 B2 | 3/2005 | Levin |
| 6,891,475 B2 | 5/2005 | Bui et al. |
| 6,925,339 B2 | 8/2005 | Grimm et al. |
| 6,998,541 B2 | 2/2006 | Morris et al. |
| 7,005,968 B1* | 2/2006 | Bridgelall .................. 340/10.42 |
| 7,044,949 B2 | 5/2006 | Orszulak et al. |
| 7,083,578 B2 | 8/2006 | Lewkowicz et al. |
| 7,118,029 B2 | 10/2006 | Nycz et al. |
| 7,154,378 B1 | 12/2006 | Ertas et al. |
| 7,213,767 B2 | 5/2007 | Tethrake et al. |
| 7,218,232 B2 | 5/2007 | DiSilvestro et al. |
| 7,237,990 B2 | 7/2007 | Deng |
| 7,253,736 B2 | 8/2007 | Tethrake et al. |
| 7,256,696 B2 | 8/2007 | Levin |
| 7,256,699 B2 | 8/2007 | Tethrake et al. |
| 7,268,684 B2 | 9/2007 | Tethrake et al. |
| 7,307,530 B2 | 12/2007 | Fabian et al. |
| 7,333,013 B2 | 2/2008 | Berger |
| 7,362,228 B2 | 4/2008 | Nycz et al. |
| 7,389,928 B2 | 6/2008 | Lubow |
| 7,420,468 B2 | 9/2008 | Fabian et al. |
| 7,421,367 B2 | 9/2008 | Nye |
| 7,443,296 B2 | 10/2008 | Mezhinsky et al. |
| 7,474,223 B2 | 1/2009 | Nycz et al. |
| 7,518,502 B2 | 4/2009 | Austin et al. |
| 7,541,933 B2 | 6/2009 | Volpi et al. |
| 7,557,710 B2 | 7/2009 | Sanchez et al. |
| 7,567,834 B2 | 7/2009 | Clayton et al. |
| 7,568,619 B2 | 8/2009 | Todd et al. |
| 7,589,634 B2 | 9/2009 | Frank |
| 7,617,137 B2 | 11/2009 | Kreiner et al. |
| 7,644,016 B2 | 1/2010 | Nycz et al. |
| 7,671,744 B2 | 3/2010 | Volpi et al. |
| 7,704,282 B2 | 4/2010 | Disilvestro et al. |
| 7,755,491 B2 | 7/2010 | Volpi et al. |
| 7,757,543 B2 | 7/2010 | Freeman et al. |
| 7,764,178 B2 | 7/2010 | Volpi et al. |
| 7,774,244 B2 | 8/2010 | Kreiner et al. |
| 7,780,590 B2 | 8/2010 | Birk et al. |
| 7,785,277 B2 | 8/2010 | Babaev et al. |
| 7,787,958 B2 | 8/2010 | Stevenson |
| 7,796,040 B2 | 9/2010 | Mezhinsky et al. |
| 7,809,184 B2 | 10/2010 | Neubauer et al. |
| 7,819,318 B2 | 10/2010 | White et al. |
| 7,837,694 B2 | 11/2010 | Tethrake et al. |
| 7,840,254 B2 | 11/2010 | Glossop |
| 7,887,559 B2 | 2/2011 | Deng et al. |
| 7,893,840 B2 | 2/2011 | Volpi et al. |
| 7,896,869 B2 | 3/2011 | DiSilvestro et al. |
| 7,916,013 B2 | 3/2011 | Stevenson |
| 7,932,825 B2 | 4/2011 | Berger |
| 7,934,648 B2 | 5/2011 | Charles et al. |
| 7,983,763 B2 | 7/2011 | Stevenson et al. |
| 7,996,286 B2 | 8/2011 | Kreiner et al. |
| 7,997,847 B2 | 8/2011 | Treat et al. |
| 8,035,487 B2 | 10/2011 | Malackowski |
| 8,054,184 B2 | 11/2011 | Cline et al. |
| 8,063,760 B2 | 11/2011 | Volpi et al. |
| 8,082,192 B2 | 12/2011 | Nycz et al. |
| 8,087,584 B2 | 1/2012 | Grimard |
| 8,105,296 B2 | 1/2012 | Morris et al. |
| 8,111,162 B2 | 2/2012 | Barnes et al. |
| 8,174,366 B2 | 5/2012 | Volpi et al. |
| 8,181,860 B2 | 5/2012 | Fleck et al. |
| 8,193,938 B2 | 6/2012 | Halberthal et al. |
| 8,196,825 B2 | 6/2012 | Turner et al. |
| 8,207,863 B2 | 6/2012 | Neubauer et al. |
| 8,233,963 B2 | 7/2012 | Hartmann et al. |
| 8,248,232 B2 | 8/2012 | Stevenson et al. |
| 8,253,555 B2 | 8/2012 | Stevenson et al. |
| 8,256,674 B2 | 9/2012 | Fleck et al. |
| 8,264,342 B2 | 9/2012 | Blair et al. |
| 8,279,068 B2 | 10/2012 | Morris et al. |
| 8,287,816 B2 | 10/2012 | Kral |
| 8,293,045 B2 | 10/2012 | Grimard |
| 8,326,414 B2 | 12/2012 | Neubardt et al. |
| 8,390,452 B2 | 3/2013 | Blake et al. |
| 8,473,074 B2 | 6/2013 | North et al. |
| 8,479,989 B2 | 7/2013 | Fleck et al. |
| 8,600,478 B2 | 12/2013 | Verard et al. |
| 8,624,721 B2 | 1/2014 | Barker, Jr. et al. |
| 8,657,174 B2 | 2/2014 | Yates et al. |
| 8,726,911 B2 | 5/2014 | Blair |
| 8,781,920 B2 | 7/2014 | Kreiner et al. |
| 8,810,405 B2 | 8/2014 | Stevenson et al. |
| 8,882,657 B2 | 11/2014 | Ohline et al. |
| 8,888,730 B2 | 11/2014 | Rossi et al. |
| 8,905,585 B2 | 12/2014 | Dallam et al. |
| 8,938,290 B2 | 1/2015 | Wingeier et al. |
| 8,968,302 B2 | 3/2015 | Weber |
| 8,985,446 B2 | 3/2015 | Fleck et al. |
| 8,994,358 B2 | 3/2015 | McElhinny et al. |
| 9,033,251 B2 | 5/2015 | Weisshaupt et al. |
| 9,050,235 B2 | 6/2015 | Blair et al. |
| 9,066,755 B1 | 6/2015 | Jacobs et al. |
| 9,067,073 B2 | 6/2015 | Simms, Jr. |
| 9,070,270 B2 | 6/2015 | Kreiner et al. |
| 9,162,001 B2 | 10/2015 | Sunkara et al. |
| 9,167,977 B2 | 10/2015 | Wingeier et al. |
| 9,204,920 B2 | 12/2015 | McPherson et al. |
| 9,370,401 B2 | 6/2016 | Sayles |
| 9,387,002 B2 | 7/2016 | Deng et al. |
| 9,414,973 B2 | 8/2016 | Fleck et al. |
| 9,486,271 B2 | 11/2016 | Dunning |
| 9,498,294 B2 | 11/2016 | Rigsby et al. |
| 9,498,647 B2 | 11/2016 | Kantrowitz et al. |
| 9,510,740 B2 | 12/2016 | Hopkins et al. |
| 2002/0032380 A1 | 3/2002 | Acker et al. |
| 2002/0032435 A1 | 3/2002 | Levin |
| 2002/0067263 A1 | 6/2002 | Tafoya et al. |
| 2004/0176683 A1 | 9/2004 | Whitin et al. |
| 2004/0215071 A1 | 10/2004 | Frank et al. |
| 2004/0267297 A1 | 12/2004 | Malackowski |
| 2005/0041966 A1 | 2/2005 | Johnson |
| 2005/0085714 A1 | 4/2005 | Foley et al. |
| 2005/0085720 A1 | 4/2005 | Jascob et al. |
| 2005/0215888 A1 | 9/2005 | Grimm et al. |
| 2006/0029186 A1 | 2/2006 | De Villiers et al. |
| 2006/0043179 A1 | 3/2006 | Nycz et al. |
| 2006/0055712 A1 | 3/2006 | Anderson |
| 2006/0094958 A1 | 5/2006 | Marquart et al. |
| 2006/0119481 A1 | 6/2006 | Tethrake et al. |
| 2006/0142656 A1* | 6/2006 | Malackowski .... A61B 17/1626 600/424 |
| 2006/0145871 A1 | 7/2006 | Donati et al. |
| 2006/0161059 A1 | 7/2006 | Wilson |
| 2006/0173291 A1 | 8/2006 | Glossop |
| 2006/0184396 A1 | 8/2006 | Dennis et al. |
| 2006/0232407 A1 | 10/2006 | Ballard |
| 2006/0235488 A1 | 10/2006 | Nycz et al. |
| 2006/0244597 A1 | 11/2006 | Tethrake et al. |
| 2006/0264742 A1 | 11/2006 | Neubauer et al. |

(56) References Cited

U.S. PATENT DOCUMENTS

| | | |
|---|---|---|
| 2007/0016009 A1* | 1/2007 | Lakin et al. .............. 600/424 |
| 2007/0125392 A1 | 6/2007 | Olson et al. |
| 2007/0160494 A1 | 7/2007 | Sands |
| 2007/0249901 A1 | 10/2007 | Ohline et al. |
| 2008/0007411 A1 | 1/2008 | Levin |
| 2008/0106419 A1 | 5/2008 | Sakama et al. |
| 2008/0120137 A1* | 5/2008 | Nyholm ............ G06Q 50/24 705/3 |
| 2008/0132882 A1 | 6/2008 | DeMaria et al. |
| 2008/0177267 A1 | 7/2008 | Sands et al. |
| 2008/0200794 A1 | 8/2008 | Teichman et al. |
| 2008/0200926 A1 | 8/2008 | Verard et al. |
| 2008/0200927 A1 | 8/2008 | Hartmann et al. |
| 2008/0231452 A1 | 9/2008 | Levin |
| 2009/0015411 A1 | 1/2009 | Li |
| 2009/0065565 A1 | 3/2009 | Cao |
| 2009/0109033 A1 | 4/2009 | Salvat |
| 2009/0267765 A1 | 10/2009 | Greene et al. |
| 2009/0281419 A1 | 11/2009 | Troesken et al. |
| 2010/0088116 A1 | 4/2010 | Eisenberg et al. |
| 2010/0262139 A1 | 10/2010 | Beller et al. |
| 2011/0121049 A1 | 5/2011 | Malinouskas et al. |
| 2011/0313894 A1 | 12/2011 | Dye et al. |
| 2012/0169470 A1 | 7/2012 | Lee |
| 2012/0296203 A1 | 11/2012 | Hartmann et al. |
| 2013/0088354 A1 | 4/2013 | Thomas |
| 2013/0181048 A1 | 7/2013 | Liu et al. |
| 2013/0218137 A1 | 8/2013 | Abovitz et al. |
| 2013/0304143 A1 | 11/2013 | Banville |
| 2014/0088570 A1 | 3/2014 | Sergeant |
| 2014/0094881 A1 | 4/2014 | Dabrowiak et al. |
| 2014/0175149 A1 | 6/2014 | Smith et al. |
| 2014/0276603 A1 | 9/2014 | Magee et al. |
| 2015/0038788 A1 | 2/2015 | Ohline et al. |
| 2015/0054625 A1 | 2/2015 | Blair et al. |
| 2015/0061834 A1 | 3/2015 | Khoury |
| 2015/0141806 A1 | 5/2015 | Smith et al. |
| 2015/0148665 A1 | 5/2015 | Sato |
| 2015/0150546 A1 | 6/2015 | Goldschmidt |
| 2015/0190202 A1 | 7/2015 | Weinert et al. |
| 2015/0216608 A1 | 8/2015 | Eschborn et al. |
| 2015/0216610 A1 | 8/2015 | Augustine |
| 2015/0265360 A1 | 9/2015 | Tatewaki et al. |
| 2015/0297306 A1 | 10/2015 | Lazar et al. |
| 2015/0302492 A1 | 10/2015 | Kreiner et al. |
| 2015/0328469 A1 | 11/2015 | Forsell |
| 2015/0351850 A1 | 12/2015 | McElhinny et al. |
| 2016/0000431 A1 | 1/2016 | Giordano et al. |
| 2016/0008091 A1 | 1/2016 | Saotome et al. |
| 2016/0038217 A1 | 2/2016 | McPherson et al. |
| 2016/0045365 A1 | 2/2016 | Foster et al. |
| 2016/0051418 A1 | 2/2016 | Fleck et al. |
| 2016/0055359 A1 | 2/2016 | Jensen et al. |
| 2016/0085922 A1 | 3/2016 | Sweeney |
| 2016/0128798 A1 | 5/2016 | Bovet et al. |
| 2016/0157868 A1 | 6/2016 | Tillman et al. |
| 2016/0157957 A1 | 6/2016 | Blair |
| 2016/0171262 A1 | 6/2016 | Fleck et al. |
| 2016/0206399 A1 | 7/2016 | Blair |
| 2016/0210548 A1 | 7/2016 | Blair |
| 2016/0212577 A1 | 7/2016 | Dor et al. |
| 2016/0220325 A1 | 8/2016 | Jeon et al. |
| 2016/0228188 A1 | 8/2016 | Sweeney |
| 2016/0250029 A1 | 9/2016 | Bonutti |
| 2016/0262847 A1 | 9/2016 | Rickert et al. |
| 2016/0270780 A1 | 9/2016 | Hall et al. |
| 2016/0283668 A1 | 9/2016 | Walker |
| 2016/0294040 A1 | 10/2016 | Blair |
| 2016/0296299 A1 | 10/2016 | Mortensen |
| 2016/0296746 A1 | 10/2016 | Wingeier et al. |
| 2016/0338778 A1 | 11/2016 | Zuhars |
| 2016/0346058 A1 | 12/2016 | Bacher et al. |
| 2016/0361127 A1 | 12/2016 | Dachs, II et al. |
| 2016/0367266 A1 | 12/2016 | Palmerton et al. |

FOREIGN PATENT DOCUMENTS

| | | |
|---|---|---|
| EP | 1719472 | 11/2006 |
| EP | 2124796 A1 | 12/2009 |
| WO | WO-2008103266 A1 | 8/2008 |

OTHER PUBLICATIONS

"Maxim", DS2505 16-kbit Add-Only Memory, instruction manual, Dallas Semiconductor [undated] (24 pages).

Hoff, et al., Automatic Tool Identification and Registration, Colorado School of Mines, Feb. 26, 2005 (8 pages).

International Search Report and Written Opinion for PCT/US2008/001977 mailed Sep. 16, 2008 claiming benefit of U.S. Appl. No. 11/708,152, filed Feb. 19, 2007.

International Search Report and Written Opinion for PCT/US2008/001992 mailed Aug. 12, 2008 claiming benefit of U.S. Appl. No. 11/708,159, filed Feb. 19, 2007.

International Search Report and Written Opinion mailed Jun. 17, 2008 for PCT/US2008/001947.

Kiefer, Automatic Recognition of Medical Instruments, Using MATLAB to recognize medical tools with the use of fiducial markings, EGES510: Multidimensional Signal and Image Processing Final Project, Dec. 12, 2005 (19 pages).

L10-USB-Pen Reader, RFID 125 KHz, Part Nr 205 0014, data sheet, Version 1.02, MBBS S.A., 2005 (1 pg).

L10-USB-Tray Reader, RFID 125 KHz, Part Nr 200 0016, data sheet, Version 1.02, MBBS S.A., 2005 (1 pg).

MediTAG™ metal 8.0, RFID 125 KHz, 2K Read/Write, Part Nr 103 0003, data sheet, Version 1.02, MBBS S.A., 2005 (1 pg).

MediTAG™ plastic 5.6, RFID 125 KHz, 2K Read/Write, Part Nr 105 0051, datasheet, Version 1.03, MBBS S.A., 2005 (1 pg).

MediTAG™ tray 70×40, RFID 125 KHz, 2K Read/Write, Part Nr 105 0059, data sheet, Version 1.03, MBBS S.A., 2005 (1 pg).

RFID, Information at the Surgeon's Fingertips, brochure, Precimed SA and MBBS SA, 2005 (6 pgs).

International Preliminary Report on Patentability and Written Opinion mailed Aug. 19, 2009 for PCT/US2008/001947 claiming benefit of U.S. Appl. No. 11/708,157, filed Feb. 19, 2007.

International Preliminary Report on Patentability and Written Opinion mailed Aug. 27, 2009 for PCT/US2008/001977 claiming benefit of U.S. Appl. No. 11/708,152, filed Feb. 19, 2007.

International Preliminary Report on Patentability and Written Opinion mailed Aug. 27, 2009 for PCT/US2008/001992 claiming benefit of U.S. Appl. No. 11/708,159, filed Feb. 19, 2007.

Office Action from corresponding European Application No. 08725561.8 dated Mar. 24, 2016.

Extended European Search Report mailed Apr. 28, 2017 in European Application No. 17155050.2.

\* cited by examiner

AUTOMATIC IDENTIFICATION OF INSTRUMENTS USED WITH A SURGICAL NAVIGATION SYSTEM

CROSS-REFERENCE TO RELATED APPLICATIONS

This application is a divisional of U.S. application Ser. No. 11/708,157 filed on Feb. 19, 2007. The disclosure of the above applications is incorporated herein by reference.

FIELD

A system for identification and information transfer regarding a surgical instrument, and particularly to a system providing specific information regarding a particular surgical instrument in a navigation system.

BACKGROUND

The statements in this section merely provide background information related to the present disclosure and may not constitute prior art.

Surgical procedures are often performed on various patients in various operating theaters at different times. Many instruments can be reused for different operations on different patients over a series of operative procedures. Also, multiple instruments can be used in a single operation procedure on a single patient. It may be desirable to provide information relating to a specific instrument or attachment to an instrument among the multiple instruments in a single operating theater, or a single procedure, or among multiple procedures with a single instrument.

Systems may be provided that allow for general tracking information to be collected relating to particular surgical instruments. The information can be transferred to a computer to determine the location of a selected instrument in an inventory, a manufacturer of an instrument, or the like. The information relating to the instrument, however, is generally limited to information relating only to inventory tracking information or limited identity information.

It is desirable, however, to provide more detailed information relating to a particular surgical instrument or attachment therefore. For example, it is desirable to ensure information relating to calibration, size, etc. are always provided and correct.

SUMMARY

A system can provide information to a surgical navigation and/or tracking system for use by the navigation system in tracking and navigating a surgical instrument. For example, calibration information, size information, configuration information, and the like can be transferred to a navigation system from a specific instrument directly. The information can include information specific to a particular procedure about a particular instrument to allow for precise tracking of the instrument during a procedure. The system can also allow for rewriting the information to insure an up-to-date information, particular procedure information, and the like are always provided and correct.

According to various embodiments, a system to determine information related to a selected member in a surgical navigation system for navigating a procedure relative to an anatomy is disclosed. The system can include a surgical instrument operable to perform a surgical procedure on the anatomy and having an identification member including selected information related to the surgical instrument and a tracking device associated with the surgical instrument. A tracking system can track a location of the tracking device. A navigation processor can determine the position of the surgical instruction based upon the tracked position of the surgical device and determine an identity of the surgical instrument based upon the identification member. Also, a display can display an icon representing the specific surgical instrument.

According to various embodiments a system to determine information related to a selected member In a surgical navigation system for navigating a procedure relative to an anatomy is taught. The system can include an information tag operable to receive and transmit selected information and an information tag reader that can at least one of read, write, or combinations thereof information of the information tag. A surgical instrument can be associated with the information tag wherein the information tag includes information specific to the surgical instrument. A navigation system can be used with a communication system that interconnects the information tag reader and the navigation system wherein information read from the information tag is transmitted to the navigation system. Also, a display can display information regarding the surgical instrument based upon the information read by the information tag reader from the information tag.

According to various embodiments a method of using a system to determine information related to a selected member in a surgical navigation system for navigating a procedure relative to an anatomy is taught. The method can include providing a surgical instrument and associating an information member with the surgical instrument. Data can be stored on the information member describing characteristics of the surgical instrument. The data from the information member can be retrieved and the retrieved data can be provided to the surgical navigation system. The provided information can be used during an operative procedure.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
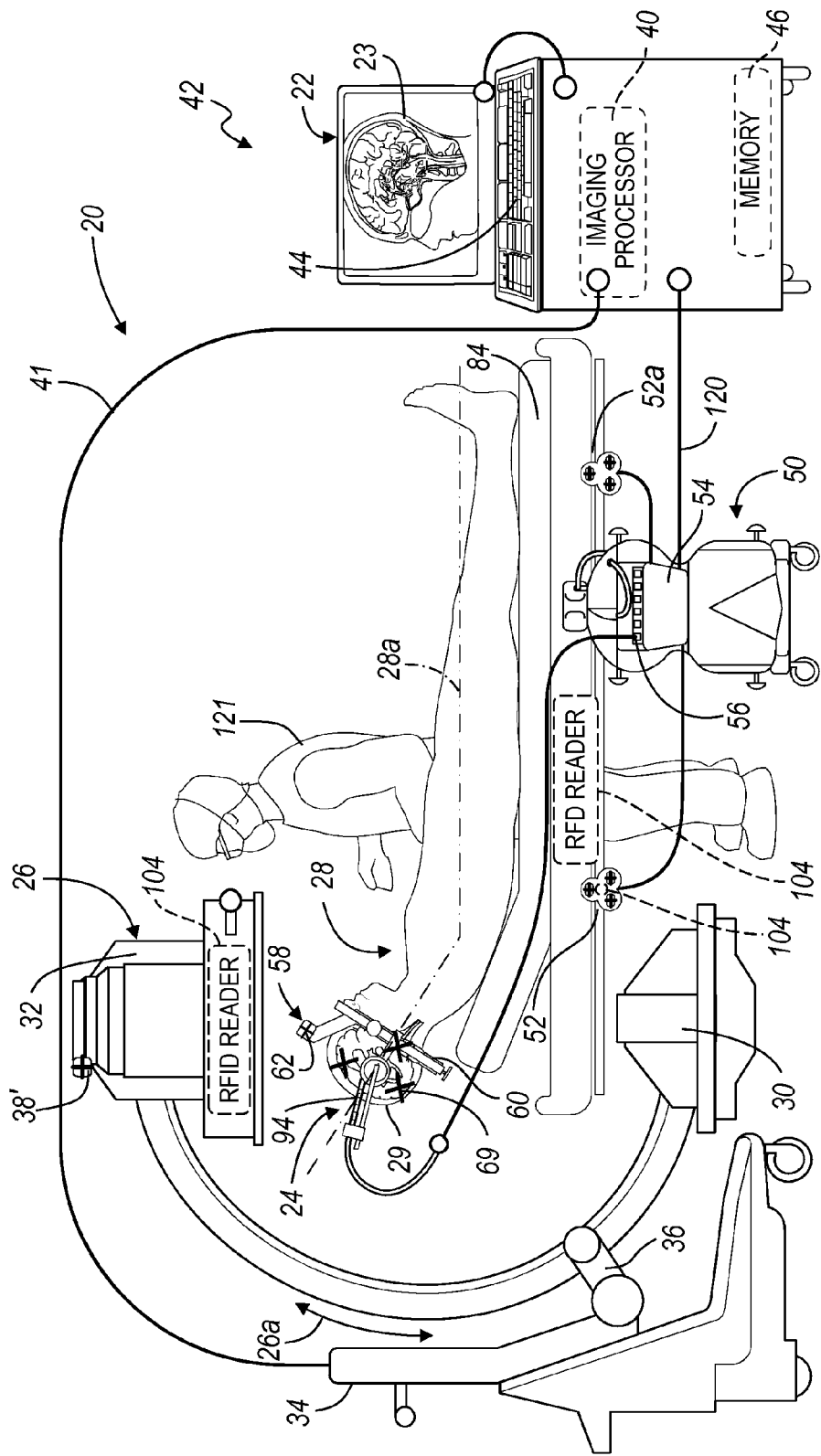
FIG. 1 is an environmental view of a surgical navigation system according to various embodiments.

A guided procedure can be performed with a navigation system 20, illustrated in FIG. 1. The guided procedure can be any appropriate procedure, such as a cardiac procedure, ENT, neural procedure, spinal procedure, and orthopedic procedure. The navigation system 20 can include various components, as will be discussed further herein. The navigation system 20 can allow a user, such as a surgeon to view on a display 22 a relative position of an instrument 24 to a coordinate system. The coordinate system can be made relative to an image, such as in an image guided procedure, or can be registered to a patient only, such as in an imageless procedure.

It should further be noted that the navigation system 20 can be used to navigate or track instruments including: catheters, probes, needles, guidewires, instruments, implants, deep brain stimulators, electrical leads, etc. Moreover, the instrument 24 can be used in any region of the body. The navigation system 20 and the various instruments 24 can be used in any appropriate procedure, such as one that is generally minimally invasive, arthroscopic, percutaneous, stereotactic, or an open procedure. Also, the instrument 24 is only exemplary of any appropriate instrument and may also represent many instruments, such as a series or group of instruments. Identity and other information relating to the instrument 24 can also be provided to the navigation system 20. Further, the information about the instrument 24 can also be displayed on the display 22 for viewing by a surgeon 121.

Although the navigation system 20 can include an exemplary imaging device 26, one skilled in the art will understand that the discussion of the imaging device 26 is merely for clarity of the present discussion and any appropriate imaging system, navigation system, patient specific data, and non-patient specific data can be used. Image data can be captured or obtained at any appropriate time with any appropriate device.

The navigation system 20 can include the optional imaging device 26 that is used to acquire pre-, intra-, or post-operative or real-time image data of a patient 28. The illustrated imaging device 26 can be, for example, a fluoroscopic x-ray imaging device that may be configured as a C-arm 26 having an x-ray source 30 and an x-ray receiving section 32. Other imaging devices may be provided such as an ultrasound system, a microscope, magnetic resonance image systems, computed tomography systems, etc. and reference herein to the C-arm 26 is not intended to limit the type of imaging device. An optional calibration and tracking target and optional radiation sensors can be provided, as understood by one skilled in the art. An example of a fluoroscopic C-arm x-ray device that may be used as the optional imaging device 26 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

An optional imaging device controller 34 can control the imaging device 26 to capture the x-ray images received at the receiving section 32 and store the images for later use. The controller 34 may also be separate from the C-arm 26 and/or control the rotation of the C-arm 26. For example, the C-arm 26 can move in the direction of arrow 26a or rotate about a longitudinal axis 28a of the patient 28, allowing anterior or lateral views of the patient 28 to be imaged. Each of these movements involves rotation about a mechanical axis 36 of the C-arm 26.

The operation of the C-arm 26 is understood by one skilled in the art. Briefly, x-rays can be emitted from an x-ray section 30 and received at a receiving section 32. The receiving section 32 can include a camera that can create the image data from the received x-rays. It will be understood that image data can be created or captured with any appropriate imaging device, such as a magnetic resonance imaging system, a positron emission tomography system, computed tomography, or any appropriate system. It will be further understood that various imaging systems can be calibrated according to various known techniques. Further, a C-arm tracking device 38 can be provided to track a position of the receiving section 32 at any appropriate time by the navigation system 20.

The image data can then be forwarded from the C-arm controller 34 to a navigation computer and/or processor 40 via a communication system 41. The communication system 41 can be wireless, wired, a data transfer device (e.g. a CD-Rom or DVD-Rom), or any appropriate system. A work station 42 can include the navigation processor 40, the display 22, a user interface 44, and a memory 46. It will also be understood that the image data is not necessarily first retained in the controller 34, but may be directly transmitted to the workstation 42 or to a tracking system 50, as discussed herein.

The work station 42 provides facilities for displaying the image data as an image on the display 22, saving, digitally manipulating, or printing a hard copy image of the of the received image data. The user interface 44, which may be a keyboard, mouse, touch pen, touch screen or other suitable device, allows a physician or user to provide inputs to control the imaging device 26, via the C-arm controller 34, or adjust the display settings of the display 22.

While the optional imaging device 26 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), T1 weighted magnetic resonance imaging (MRI), T2 weighted MRI, high frequency ultrasound (HIFU), positron emission tomography (PET), optical coherence tomography (OCT), intra-vascular ultrasound (IVUS), ultrasound, intra-operative CT, single photo emission computed tomography (SPECT), or planar gamma scintigraphy (PGS) may also be used to acquire 2D, 3D or 4D pre- or post-operative and/or real-time images or image data of the patient 28. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, can also provide functional image data superimposed onto anatomical data to be used to confidently reach target sites within the patient 28. It should further be noted that the optional imaging device 26, as shown in FIG. 1, provides a virtual bi-plane image using a single-head C-arm fluoroscope as the optional imaging device 26 by simply rotating the C-arm 26 about at least two planes, which could be orthogonal planes to generate two-dimensional images that can be converted to three-dimensional volumetric images. By acquiring images in more than one plane, an icon representing the location of an impacter, stylet, reamer driver, taps, drill, deep brain stimulators, electrical leads, needles, implants, probes, or other instrument, introduced and advanced in the patient 28, may be superimposed in more than one view on the display 22 allowing simulated bi-plane or even multi-plane views, including two and three-dimensional views.

With continuing reference to FIG. 1, the navigation system 20 can further include the tracking system 50 that includes a localizer 52 (e.g. a coil array or multiple coil arrays), a coil array controller 54, a navigation interface 56 for an instrument tracking device and a dynamic reference frame 58. The dynamic reference frame 58 can include a dynamic reference frame member or holder 60 and a removable tracking device 62. Alternatively, the dynamic reference frame 58 can include a tracking device that is formed integrally with the dynamic reference frame member 60. One skilled in the art will understand that the tracking device 62 can be any appropriate device that can be an emitter, a receiver, a reflector, a sensor to sense a field, or any other appropriate device that can be tracked by a tracking system including a localizer.

The transmitter coil array 52 may also be supplemented or replaced with a second localizer 52a. The second localizer 52a may be one such as that described in U.S. patent application Ser. No. 10/941,782, filed Sep. 15, 2004, now U.S. Pat. App. Pub. No. 2005/0085720, and entitled "METHOD AND APPARATUS FOR SURGICAL NAVIGATION", herein incorporated by reference. As is understood the localizer array can transmit signals that are received by the dynamic reference frame 58, and a tracking device 94. The dynamic reference frame 58 and the tracking device 94 can then transmit signals based upon the received signals from the array 52, 52a.

It should further be noted that the entire tracking system 50 or parts of the tracking system 50 may be incorporated into the imaging device 26. For example, one of the localizers can be incorporated into the imaging device 26. Incorporating the tracking system 50 may provide an integrated imaging and tracking system. Any combination of these components may also be incorporated into the imaging system 26, which can include any appropriate imaging device.

The transmitter coil array 52 can be attached to the receiving section 32 of the C-arm 26. It should be noted, however, that the transmitter coil array 52 may also be positioned at any other location as well. For example, the transmitter coil array 52 may be positioned at the x-ray source 30, within or atop an operating room (OR) table 84 positioned below the patient 28, on siderails associated with the OR table 84, or positioned on the patient 28 in proximity to the region being navigated, such as on the patient's chest. The coil array 52 can be used in an electromagnet tracking system as the localizer therefore. The transmitter coil array 52 may also be positioned in the items being navigated, further discussed herein. The transmitter coil array 52 can include a plurality of coils that are each operable to generate distinct electromagnetic fields into the navigation region of the patient 28, which is sometimes referred to as patient space. Electromagnetic systems are generally described in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 52 is controlled or driven by the coil array controller 54. The coil array controller 54 drives each coil in the transmitter coil array 52 in a time division multiplex or a frequency division multiplex manner. In this regard, each coil may be driven separately at a distinct time or all of the coils may be driven simultaneously with each being driven by a different frequency, as discussed further herein. Upon driving the coils in the transmitter coil array 52 with the coil array controller 54, electromagnetic fields are generated within the patient 28 in the area where the medical procedure is being performed, which is again sometimes referred to as patient space. The electromagnetic fields generated in the patient space induce currents in the tracking devices 62, 94 positioned on or in the instruments 24. These induced signals from the instrument 24 are delivered to the navigation device interface 56 and can be forwarded to the coil array controller 54. The navigation device interface 54 may provide all the necessary electrical isolation for the navigation system 20, as discussed herein. The navigation device interface 56 can also include amplifiers, filters and buffers to directly interface with the tracking devices 62, 94 in the instrument 24. Alternatively, the tracking devices 62, 94, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled with a physical cord to the navigation device interface 56.

When the navigation system 20 uses an EM based tracking system, various portions of the navigation system 20, such as tracking devices 62, 94, that can be associated with the (DRF) 58 and the instrument 24, are equipped with at least one, and generally multiple coils that are operable with the EM localizer arrays 52, 52a. Alternatively, the tracking system 50 may be a hybrid system that includes components from various tracking systems such as optical, acoustic, radiation, radar, etc.

Figure 3:
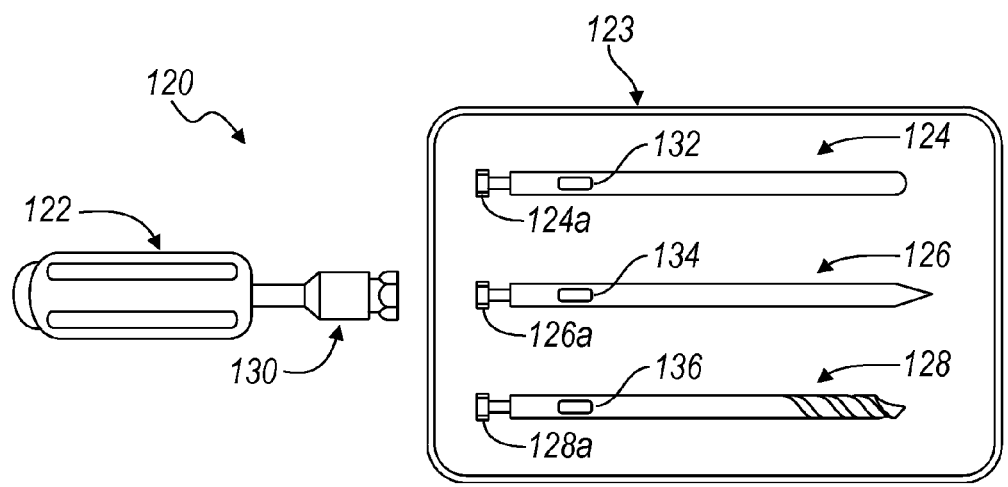
FIG. 3 is an illustration of a multi-piece surgical system.

The tracking device 94 on the instrument 24 can be in a handle 122 (FIG. 3) or inserter that interconnects with an attachment 124, 126, 128 (FIG. 3). The instrument 24 may assist in placing a screw implant 142, 144, 146 (FIG. 4), a prosthesis 147 (FIG. 4), or driving a selected portion. The instrument 24 can include a graspable or manipulable portion at a proximal end and the tracking sensor device and can be fixed near the manipulable portion of the instrument 24 or at a distal working end, as discussed herein. The tracking device 24 can include an electromagnetic sensor to sense the electromagnetic field generated by the transmitter coil array 52 that can induce a current in the tracking device 94.

The dynamic reference frame 58 of the tracking system 50 can also be coupled to the navigation device interface 56 to forward the information to the coil array controller 54. The dynamic reference frame 58, according to various embodiments, may include a small magnetic field detector as the tracking device 62. The dynamic reference frame 58 may be fixed to the patient 28 adjacent to the region being navigated so that any movement of the patient 28 is detected as relative motion between the transmitter coil array 52 and the dynamic reference frame 58. The dynamic reference frame 58 can be interconnected with the patient 28 in any appropriate manner, including those discussed herein. Any relative motion is forwarded to the coil array controller 54, which updates registration correlation and maintains accurate navigation, further discussed herein. If the dynamic reference frame 58 is electromagnetic it can be configured as a pair or trio of orthogonally oriented coils, each having the same center or may be configured in any other non-coaxial or co-axial coil configurations.

The dynamic reference frame 58 may be affixed externally to the patient 28, adjacent to the region of navigation, such as on the patient's cranium, etc., as shown in FIG. 1. The dynamic reference frame 58 can be affixed to the patient's skin, by way of a selected adhesive patch and/or a tensioning system. The dynamic reference frame 58 may also be removably attachable to a fiducial marker 69. The fiducial markers can be anatomical landmarks or members attached or positioned on the patient's 28 body. The dynamic reference frame 58 can also be connected to a bone portion of the anatomy. The bone portion can be adjacent the area of the procedure, the bone of the procedure, or any appropriate body portion.

Although the discussion above is directed to an electromagnetic navigation and tracking system, it will be understood that any appropriate tracking system can be used as the tracking system 50. For example, one skilled in the art will understand that an optical tracking system can be used, a radar tracking system can be used, an acoustic tracking system can be used, an accelerometer tracking system can be used, or any appropriate tracking system. Nevertheless, the tracking system can include any appropriate portions such as an appropriate localizer for the tracking system and appropriate tracking devices for the tracking system. Thus, the discussion herein regarding an electromagnetic tracking system is merely exemplary of any appropriate tracking system.

Briefly, the navigation system 20 operates as follows. The navigation system 20 creates a translation map between all points in the image data or image space and the corresponding points in the patient's anatomy in patient space. After this map is established, the image space and patient space are registered. In other words, registration is the process of determining how to correlate a position in image space with a corresponding point in real or patient space. This can also be used to illustrate a position of the instrument 24 relative to the proposed trajectory and/or the determined anatomical target. The work station 42 in combination with the coil array controller 54 and the C-arm controller 34 identify the corresponding point on the pre-acquired image or atlas model relative to the tracked instrument 24 and display the position on display 22 and relative to the image data 23. This identification is known as navigation or localization. An icon representing the localized point or instruments is shown on the display 22 within several two-dimensional image planes, as well as on three and four dimensional images and models.

To register the patient 28 the surgeon 121 may use point registration by selecting and storing particular points from the pre-acquired images and then touching the corresponding points on the patient's 28 anatomy with a pointer probe or any appropriate tracked device, such as the instrument 24. The navigation system 20 analyzes the relationship between the two sets of points that are selected and computes a match, which allows for a determination of a correlation of every point in the image data or image space with its corresponding point on the patient's anatomy or the patient space.

The points that are selected to perform registration or form a translation map are the fiducial markers 69, such as anatomical or artificial landmarks. Again, the fiducial markers 69 are identifiable on the images and identifiable and accessible on the patient 28. The fiducial markers 69 can be artificial landmarks that are positioned on the patient 28 or anatomical landmarks that can be easily identified in the image data. The artificial fiducial markers 69, can also form part of the dynamic reference frame 58, such as those disclosed in U.S. Pat. No. 6,381,485, entitled "Registration of Human Anatomy Integrated for Electromagnetic Localization," issued Apr. 30, 2002, herein incorporated by reference. It will be understood that the "X" illustrated in FIG. 1 can merely indicate a position of a fiducial marker 69 rather than being the fiducial marker 69.

The system 20 may also perform registration using anatomic surface information or path information as is known in the art (and may be referred to as auto-registration). The system 20 may also perform 2D to 3D registration by utilizing the acquired 2D images to register 3D volume images by use of contour algorithms, point algorithms or density comparison algorithms, as is known in the art. An exemplary 2D to 3D registration procedure is set forth in U.S. Ser. No. 10/644,680, filed on Aug. 20, 2003, now U.S. Pat. App. Pub. No. 2004-0215071, entitled "Method and Apparatus for Performing 2D to 3D Registration", hereby incorporated by reference.

In order to maintain registration accuracy, the navigation system 20 continuously can track the position of the patient 28 during registration and navigation with the dynamic reference frame 58. This is because the patient 28, dynamic reference frame 58, and transmitter coil array 52 may all move during the procedure, even when this movement is not desired. Alternatively the patient 28 may be held immobile once the registration has occurred, such as with a head frame. Therefore, if the navigation system 20 did not track the position of the patient 28 or area of the anatomy, any patient movement after image acquisition would result in inaccurate navigation within that image. The dynamic reference frame 58 allows the tracking system 50 to track the anatomy and can assist in registration. Because the dynamic reference frame 58 is rigidly fixed to the patient 28, any movement of the anatomy or the transmitter coil array 52 is detected as the relative motion between the transmitter coil array 52 and the dynamic reference frame 58. This relative motion is communicated to the coil array controller 54, via the navigation probe interface 56, which updates the registration correlation to thereby maintain accurate navigation.

The dynamic reference frame 58 can be affixed to any appropriate portion of the patient 28, and can be used to register the patient space to the image data, as discussed above. For example, when a procedure is being performed relative to a cranium 29, the dynamic reference frame 58 can be interconnected with the cranium 29. The dynamic reference frame 58 can be interconnected with the cranium 29 in any appropriate manner, such as those discussed herein according to various embodiments.

Navigation can be assisted with registration and the navigation system 20 can detect both the position of the patient's anatomy and the position of the device 58 or attachment member (e.g. tracking sensor 94) attached to the instrument 24. Knowing the location of these two items allows the navigation system 20 to compute and display the position of the instrument 24 or any portion thereof in relation to the patient 28. The tracking system 50 is employed to track the instrument 24 and the anatomy 28 simultaneously.

The tracking system 50, if it is using an electromagnetic tracking assembly, can work by positioning the transmitter coil array 52 adjacent to the patient space to generate a magnetic field, which can be low energy, generally referred to as a navigation field. Because every point in the navigation field or patient space is associated with a unique field strength, the electromagnetic tracking system 50 can determine the position of the instrument 24 by measuring the field strength at the tracking device 94 location. The dynamic reference frame 58 is fixed to the patient 28 to identify the location of the patient 28 in the navigation field. The electromagnetic tracking system 50 continuously recomputes the relative position of the dynamic reference frame 58 and the instrument 24 during localization and relates this spatial information to patient registration data to enable image guidance of the instrument 24 within and/or relative to the patient 28.

To obtain maximum accuracy it can be selected to fix the dynamic reference frame 58 in each of at least 6 degrees of freedom. Thus, the dynamic reference frame 58 or any of the tracking sensors 258 can be fixed relative to axial motion X, translational motion Y, rotational motion Z, yaw, pitch, and roll relative to the portion of the patient 28 to which it is attached. Any appropriate coordinate system can be used to describe the various degrees of freedom. Fixing the dynamic reference frame relative to the patient 28 in this manner can assist in maintaining maximum accuracy of the navigation system 20.

The instrument 24 can be any appropriate instrument (e.g., a catheter, a probe, a guide, etc.) and can be used for various procedures and methods, such as delivering a material to a selected portion of the patient 28, such as within the cranium 29. Other exemplary instruments can also be implantable members, scissors, clamps, retractors, etc. The material can be any appropriate material such as a bioactive material, a pharmacological material, a contrast agent, or any appropriate material. As discussed further herein, the instrument 24 can be precisely positioned via the navigation system 20 and otherwise used to achieve a protocol for positioning the material relative to the patient 28 in any appropriate manner, such as within the cranium 29. The instrument 24 may also include a brain probe to perform deep brain stimulation.

Figure 2:
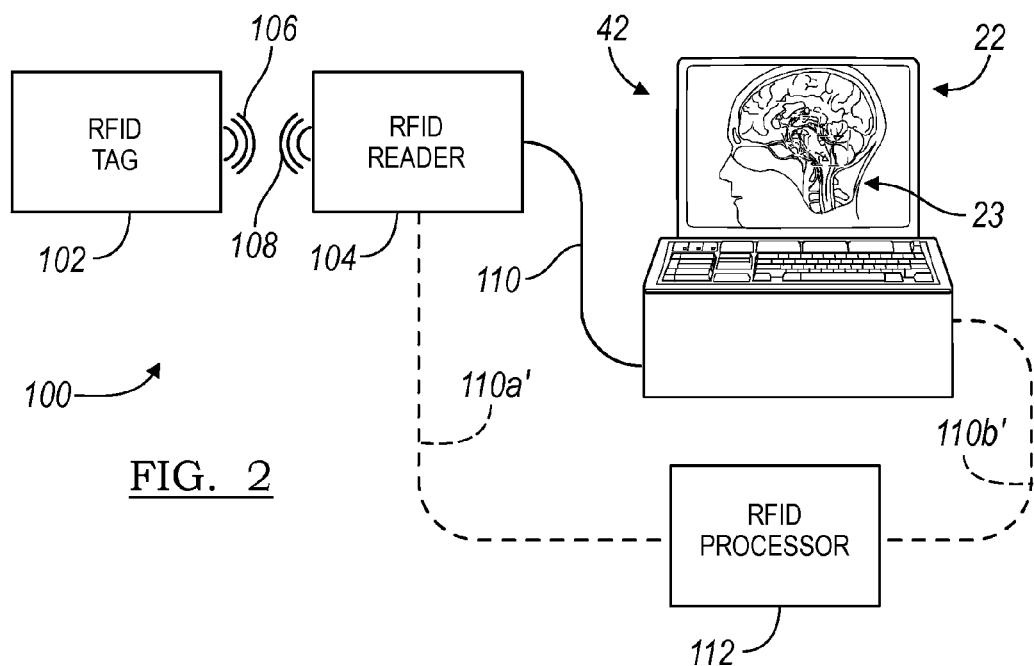
FIG. 2 is a detailed block diagram of an information reading system according to various embodiments.

Determination of or information relating to the current instrument 24 at any point in time can assist the navigation system 20 in displaying an appropriate location or icon on the display 22. For example, an icon representing a particular instrument can be used as well as an exact size or shape of the particular instrument. Therefore, an instrument identification system according to various embodiments is taught. The navigation system 20 can be used with an identification system 100, as illustrated in FIG. 2. The identification system 100 can include a radio frequency identification (RFID) or information system. Such RFID systems include those sold by Precimed, Inc. of Exton, Pa. or MBBS S.A. of Cocelles, Switzerland.

The RFID identification system 100 can generally include an information RFID tag or member 102 and an RFID reader 104. The RFID tag 102 can transmit or be induced to transmit a signal 106 that can be received as a reception signal 108 by the RFID reader 104. The signal induced or sent by the RFID tag 102 can be any appropriate signal, such as one that is induced by a power signal from the RFID reader 104, a signal powered by an onboard system in the RFID tag 102, or any appropriate manner. The RFID reader 104 can be interconnected through a communication line 110 with the workstation 42. It will be understood, however, that a wireless system can also be used to transmit information from the RFID reader 104 to the work station 42.

Returning reference to FIG. 1, the RFID reader 104 can be provided in any appropriate location in an operating theater. For example, the RFID reader 104 can be integrated with the localizer array 52 (shown in plantom). Also, the RFID reader 104 can be integrated into the bed 84, the array 52, or any appropriate location. Although multiple RFID readers can be provided, an RFID reader can be provided with the localizer array 52 to insure that an instrument that is in the navigation field is the appropriate instrument or is being appropriately illustrated on the display 22. Therefore, the RFID reader 104 can be provided in any appropriate location within an operating theater.

As discussed above, the localizer array 52 can include electromagnetic coils that can send or receive electromagnetic fields. Therefore, according to various embodiments, the coils provided in the localizer array 52 can also serve as the RFID reader 104. Therefore, not only can the RFID reader 104 be integrated with the localizer array 52, the localizer array 52 can act as the RFID reader 104, according to various embodiments. This can be provided if the RFID tags 102 are provided to transmit or receive on the appropriate frequencies used with the coil array 52.

An RFID processor 112 can also be provided in the communication line 110A' and 110B' between the RFID reader 104 and the workstation 42. The RFID processor 112 can be used to process the signal from the RFID reader 104 for interpretation by a processor on the work station 42. Therefore, the processor provided in the work station 42 can be selected to simply execute instructions related to the information provided from the RFID processor 112. It will be understood, however, that the RFID processor 112 can be provided as a single unit with the RFID reader 104 or can be provided in the work station 42 according to various embodiments.

The RFID tag 102 can be provided on any appropriate portion that can be used in an operating theater, and can include any appropriate tag. For example, RFID tags can include those provided by MBBS of Switzerland. The RFID tag 102 can be programmed with a certain amount and type of information or data at any appropriate time. For example, a selected information can be programmed or stored at manufacturing or at integration of the RFID tag 102 with the instrument 24. The information can include any appropriate information, such as size of the instrument 24, material of manufacturing, manufacturing information, and the like. The RFID tag 102 can also be provided with a mechanism to change or add information at a later time. For example, a calibration change or orientation change can occur and can alter the correctness of the information on the RFID tag 102 after manufacturing.

Figure 6A:
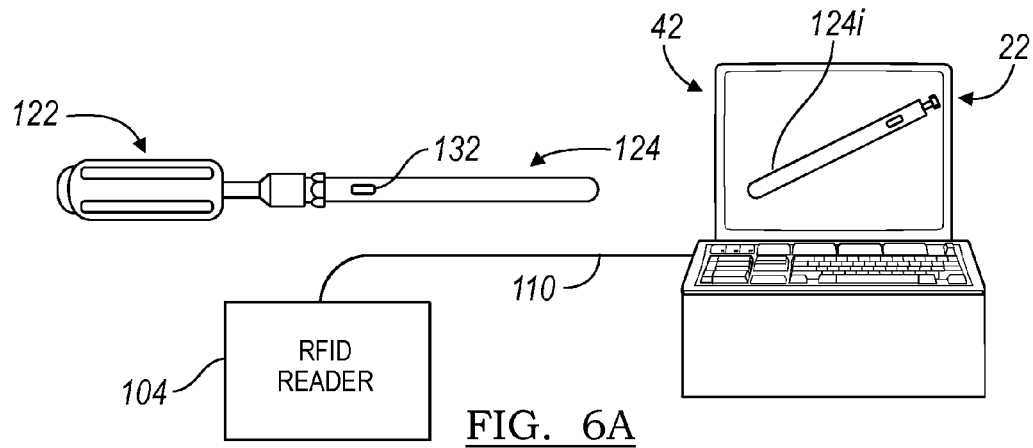
FIG. 6A illustrates an information reader and a display according to various embodiments.
Figure 6B:
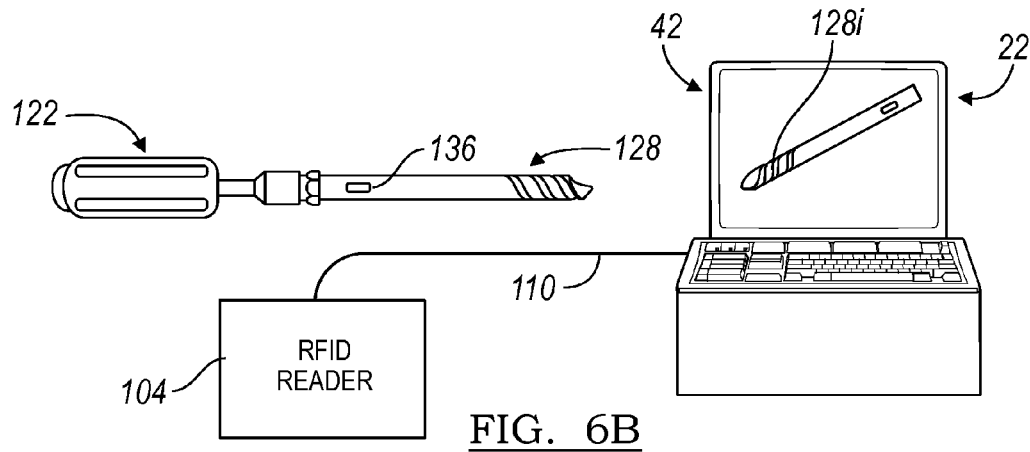
FIG. 6B illustrates an information reader and a display according to various embodiments.

With reference to FIG. 3, an instrumentation set 120 can be used as the instrument 24 and can be used with the identification system 100. The instrumentation set 120 can include numerous components, such as a handle 122 and a working or interchangeable portion 123 including a probe 124, an awl 126, and a tap 128. The instrument system 120 can be used for a single procedure on a single patient or between multiple patients in multiple procedures. Nevertheless, the working portion 123 of the system 120 can include each of the probe 124, the awl 126, and the tap 128. Each of the working portions 123 can include quick connect portions 124a, 126a, and 128a for each of the respective components. The working portion 123 can be interconnected with a quick connect portion 130 of the handle 122 during an operating procedure. If the working portion 123 is being navigated on the display 22 or displayed relative to the image data 23, the particular working portion 123 may be selected to be particularly illustrated on the display 22 (FIGS. 6A and 6B). Further, each of the various working portions 123, can include different dimensions, such as lengths, diameter, angles, configurations and the like. The specific information relating to each of the particular working portions 123 can also be specifically displayed or illustrated on the display 22 at a selected time, as discussed herein.

The many different types of information that can be stored or saved on the RFID tag 102 can include calibration information which can include different instrument specific information. For example, the position of a tip of the instrument 24 can be saved or stored on the RFID tag 102 which can also include a length of the instrument, to determine a position of the tip of the instrument 24. Also, other information regarding calibration can include a configuration, an angle, an orientation, or the like. The calibration information saved on the RFID tag 102 can include specific information that can be used for various purposes, such as being displayed on the display 22 (FIG. 6A-FIG. 6B). As discussed further herein the calibration information, that includes information such as size and tip location, can be used to determine an appropriate icon or appropriate rendering of the instruments being displayed on the display 22.

During an operative procedure, interconnecting the selected working portion 123 with the handle 122 can be displayed on the display 22 by the reading of the particular RFID tag 102 on one of the working portion 123. In this regard, each of the working portion 123 can include an RFID tag 102, such as a first RFID tag 132 on the probe 124, a second RFID tag 134 on the awl 126, and a third RFID tag 136 on the tap 138. The multiple RFID tags 132-136 can provide specific information for the parts 124-128 of the working portion 123 to which they are attached. The RFID reader 104 can be used to read the RFID tag 132-136 interconnected with a particular working portion 123. The RFID reader 104 can be provided in any appropriate manner, including that discussed further herein. Nevertheless, particular information can be provided on the RFID tags 132-136 for use by the navigation system 20 to assist in navigating the instrument 24. As discussed above, the information can include length, diameter, angle, and the like of the working portion 123.

Further, various additional information can be added to the particular RFID tags 102 at a selected time. For example, each time the particular instrument is used in a procedure it can be selected to determine or write to the RFID tag 132-136 that a particular procedure has been performed with the particular instrument. Therefore, a lifetime or number of work cycles of the particular working portion can be stored on the different RFID tag 132-136 and be specifically determined for each of the individual working member 123.

Exemplary information can include a calibration information that can be provided regarding one particular instrument, including the length, diameter and the like of the instrument. Because of a writing capability, a user can select to change or recalibrate the information on the RFID tag 102 regarding the particular working portion 123. For example, the probe 124 may change over a life span of the probe 124. Although the change in the probe 124 can change its length, angle, or the like, it can still be usable. Therefore, calibration information relating to the particular probe 124 can be read and rewritten to the first RFID tag 132.

As one skilled in the art will understand, the position of various instruments can be used to assist in navigating or tracking an instrument relative to the patient 28. Further, various information can be determined intraoperably, such as a length of a particular tool, particularly when the tracking device 94 is attached intraoperatively. For example, the tracking device can be interconnected with the instrument 24 and can be intraoperatively calibrated by touching a reference point, such as a portion of the DRF 58. The tracking system 50 can then determine a position of the tracking device 94 relative to a tip of the instrument 24. It will be understood that this information can also be written to the RFID tag 102, if selected. Nevertheless, the position of the tracking device 94 may be moved from operation to operation, thus providing such calibration information from a calibration performed intraoperatively may or may not be written, and can depend on various conditions.

Nevertheless, further calibration information can be provided to the RFID tag 102 at any appropriate time. The calibration information can include size, tip location, angulations or orientation of the instrument 24, or any other appropriate information. It will be understood that the information can generally be used by the navigation system 20 for display on the display 22. As discussed further herein, the calibration information can be used to select an appropriate icon, render an appropriate icon, determine the location of a portion of the icon relative to a particular part of the image data 23, or other appropriate information.

The identity of the particular working portion 123 can be encoded or stored on the RFID tags 132-136. The particular identification of the working portion 123 can be provided to the navigation system 20 for various appropriate purposes. As discussed above, the navigation system 20 can be used to navigate a procedure relative to the patient 28. Further, the navigation system 20, or any appropriate system, can be used to plan a procedure relative to the patient 28. The planned procedure can be provided with a navigation system 20 or loaded onto the navigation system 20 for use during a procedure on the patient 28. As part of the plan, the identity of instruments to be used on the patient 28 can be included in the plan that is provided on the navigation system 20. Thus, during an actual procedure, the identity of the particular working portion 123 provided for a use on the patient 28 can be verified.

Figure 4:
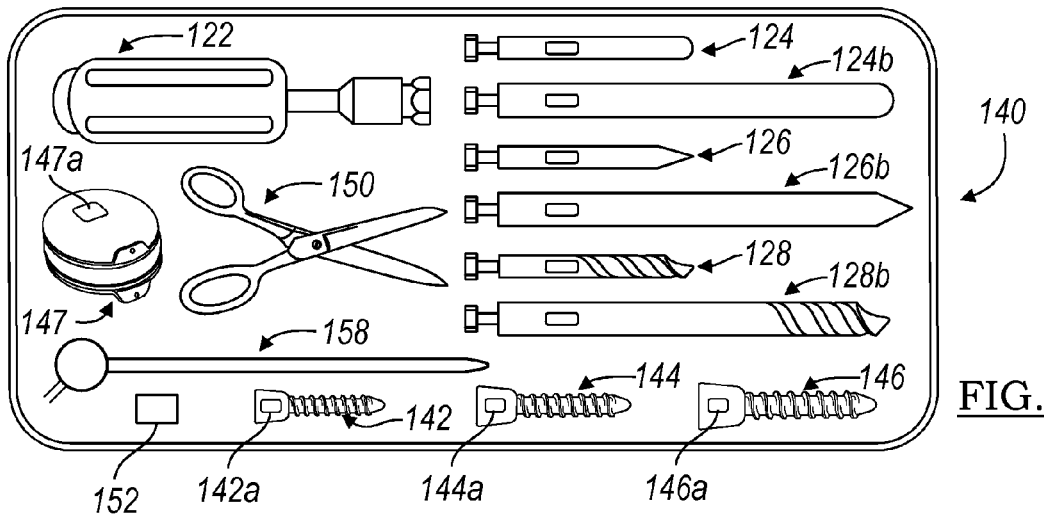
FIG. 4 is an illustration of multi-piece surgical system according to various embodiments.

With reference to FIG. 4, a kit for a surgical procedure 140 is illustrated. The kit 140 can include various portions, such as the handle 122, the working portions 123, including various lengths, such as a first length probe 124A, and a second length of a probe 124B, two lengths of awls 126A, 126B and two lengths of taps 128A, 128B. Further additional portions can be provided by the kit 140, such as implants of various lengths 142, 144, and 146. The implants 142-146 can also be different types of implants, different sizes of implants, or the like. Also, a stylet 148 can be provided along with any other appropriate instruments, such as a scissor 150.

Each of the multiple instruments or portions of the kit 140 can be provided with a specific RFID tag, as discussed above. Further, a tray RFID tag 152 can also be provided. The multiple RFID tags can be read with the RFID reader 104 and the information transferred to the work station 42. Thus, prior to a procedure, verification of particular instruments, particular implants, or the like can be provided to the work station 42 for verification by a user, such as the surgeon 121 or a nurse, before opening or breaking the sterility of the kit 140. Further, the verification of the appropriate instrument or working portions 123 can be provided before opening the kit 140 or beginning a procedure on the patient 28 by being compared to a plan stored in the workstation 42. The RFID tags, including the tray RFID tag 152 can be provided to insure that an appropriate system, instrument, or implant is being provided for a particular procedure on a particular patient.

As discussed above, the plan for a particular patient or a procedure can be provided in the work station 42. Therefore, once the RFID reader has read the RFID tags provided in the kit 140, the plan, such as an instrument table stored as a part of the plan, can be used to confirm the presence of the appropriate instrument or implants. Also, this can allow a period to obtain a different or appropriate instrument or implants if they are needed. This also can provide an error check or confirmation for a particular procedure.

The kit 140 can include the implants 142, 144, 146, and 147. The implants can be the same, such as implants 142-146 in different sizes, or can include a different implant, such as a spinal implant 147. Nevertheless, each of the implant portions can include a respective RFID tag or identification member 142a, 144a, 146a, and 147a. Like the RFID tags that are provided for each of the various instruments, the RFID tags 142a, 144a, 146a, and 147a on each of the implants 142-147 can be read with the RFID reader 104. Briefly, this can allow the determination or verification of an appropriate implant being used at a particular time, such as within a particular step of the plan for the procedure.

In addition, the RFID tags 142a-147a, can be used to ensure that appropriate implants are provided in the kit 140. Also, the RFID tags on the implants can be used in a post-operative survey to ensure that all of the appropriate implants are positioned in the patient as defined by the pre-operative plan or by the surgeon intra-operatively. Therefore, one skilled in the art will understand that the RFID tags can be provided on the implants as well as the instruments for various purposes, such as identification and verification.

Figure 5:
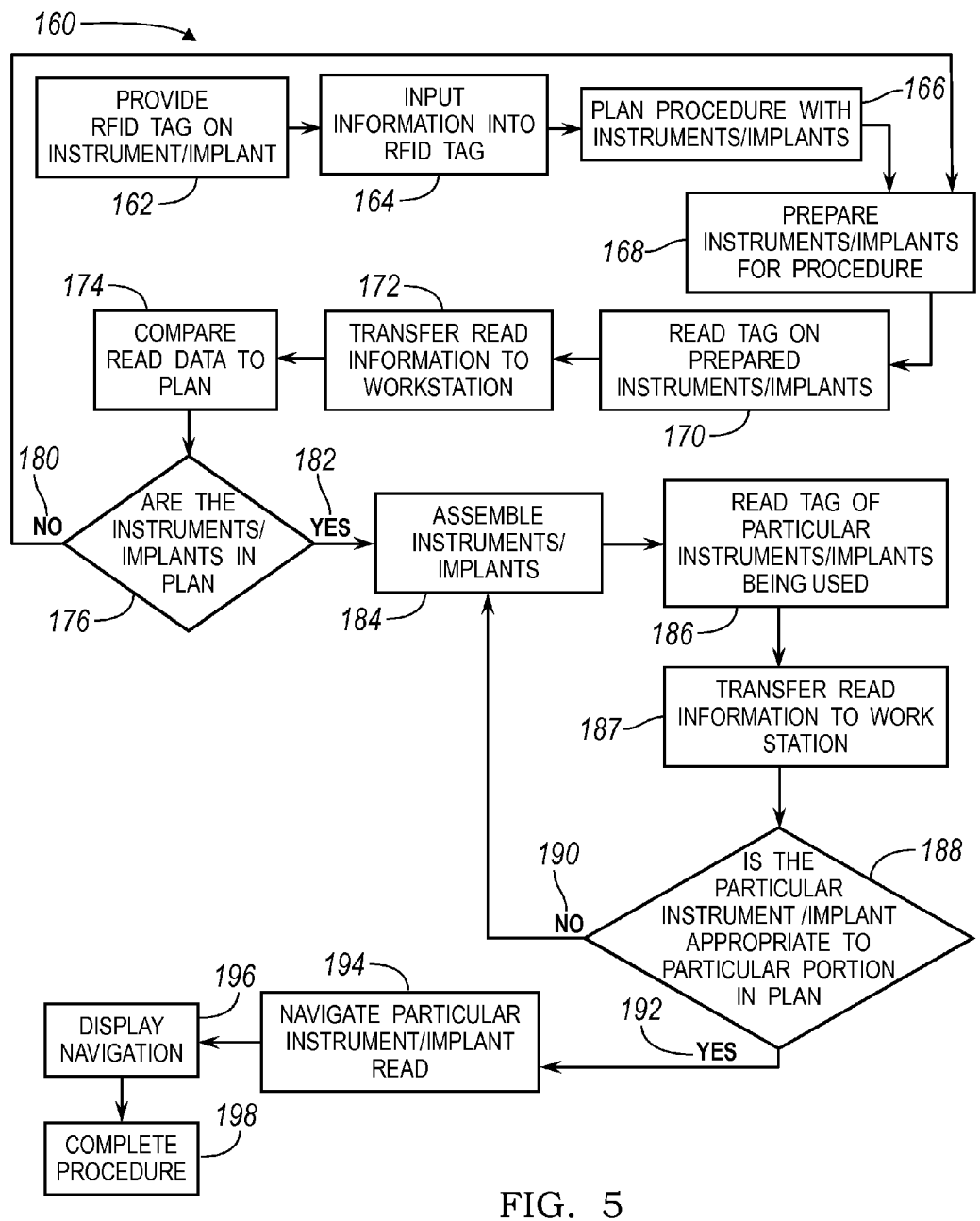
FIG. 5 is a flow chart of a method according to various embodiments for transferring information.

With reference to each of the Figures above, and additional reference to FIG. 5, an exemplary system or method is illustrated in a flow chart 160. The flow chart 160 is only an exemplary method, and is provided merely to illustrate the system according to various embodiments for use with a navigation system. The RFID tags can be provided on various instruments and implants in block 162. Various information can be input into the RFID tag in block 164. As discussed above, the particular information stored on the RFID tag can include calibration information, length information, size information, manufacturing information, or any appropriate type of information. Further, the information stored into the RFID tag can be written at any appropriate time, as discussed above. For example, the information can be provided during a particular procedure, subsequent to a particular procedure, or at any appropriate time. The information written into the RFID tag can include information changed by a particular user or by a supplier, manufacturer, or the like.

A procedure can then be planned with particular instruments or implants in block 166. The procedure planned in block 166 can include any appropriate procedure, such as a neurological procedure, an orthopaedic procedure, a cardiac procedure, or the like. For example, a procedure can include a spinal implant, an ablation, a resection, or the like. The procedure planned in block 166 can also include the acquisition of image data of the patient 28 or any other appropriate information. Further, the procedure planned in block 166 can also include determining the appropriate instruments and implants for a particular procedure. The particular instruments and implants can be provided as part of the plan for input into the navigation system 20, including the work station 42. The planned procedure in block 166, therefore, can include any appropriate information and can include particular information for a specific planned procedure. It will be understood that the plan made in block 166 can be altered at any appropriate time by an appropriate individual, such as the user 121. Providing the plan 166, however, can be used to insure that a procedure actually performed substantially matches or adheres to a planned procedure.

Once the plan has been produced in block 166 and the information of various implants or instruments are provided on various RFID tags to provided therewith, the instruments and implants can be prepared for the procedure or plan in block 168. Preparing the implants and the instruments for the procedure can include any appropriate preparation, such as obtaining them, providing them in a tray, sterilizing the implants, preparing patient specific implants, or the like. The instruments prepared for the procedure block 168, however, can then be provided to an operating theater for the planned procedure. Providing the implants and the instruments to the operating theater can include any appropriate step, such as moving a sterilized tray or container to an operating theater for use by a particular user, such as the surgeon 121.

Once the instruments and implants are provided to the operating theater, the RFID tags on the instruments and implants can be read in block 170. The information read in block 170 can be read with the RFID reader 104, discussed above, or with any appropriate system. Further, as discussed above, the RFID reader 104 can be integral with the navigation system 20, including a separate reader, or be provided in any appropriate manner. The information read from the RFID tags in block 170, however, can be transferred to the work station 42 in block 172. The information transferred to the work station can be transferred in any appropriate manner, including the transmission line 110 discussed above, a wireless system, a hard disk or hard media, or in any appropriate manner.

Nevertheless, the information read from the RFID tags in block 170 can be transferred to the work station 42 for any appropriate purpose. For example, the data read from the tags on block 170 and transferred in block 172 can be compared to the plan from block 166 in block 174. Comparing the plan in block 174 can include insuring that each of the appropriate instruments and implants have been provided and prepared in block 168. Therefore, the comparison in block 174 can be to insure that all the appropriate instruments, all the appropriate preparation of instruments or implants, or any other preparation has occurred and each are being provided to the operating theater.

A decision block 176 can be used to insure that each appropriate instrument and implant is being provided to the operating theater. When comparing the information that is transferred to the work station from block 174, the decision block 176 can be used to insure that all of the appropriate instruments and implants are provided to an operating theater. If the determination is NO in, block 180, different or additional instruments can be prepared in block 168. Therefore, the procedure 160 can be part of a process to insure that each of the appropriate instruments and implants are provided to an operating theater. Generally, at least this portion, determining that the instruments and implants are appropriate for the plan, can be performed before the patient 28 is prepped for a procedure. Although it can be understood that the determination can occur at any time, it can be selected to insure that the appropriate instruments and implants are provided in a selected manner prior to exposing the patient 28 to the operating theater or an operating procedure. The other alternative is YES in block 182, which can allow the procedure to continue.

Once it has been determined that each of the appropriate implants and instruments are provided, the implants and instruments can be assembled in a selected manner in block 184. The assembly of the instruments and implants can be in any appropriate manner, such as interconnecting a working portion 123 with the handle 122. The assembly of the instruments or the implants can be used to perform a selected portion of the procedure or plan, as discussed above.

The information from the RFID tag from a selected or active instrument can be read in block 186. As discussed above, the RFID reader 104 can be provided in the operating theater, such that when the interconnection of an instrument or implant is performed, the RFID reader 104 can also confirm that the appropriate instrument or implant has been assembled or is being provided relative to the patient 28 according to the plan in block 166. The active instrument is generally one or more instruments about to be used in the procedure and in or near parent space. The information can be read from the RFID tag at any appropriate time, such as when an RFID tag is moved into the navigation field. As discussed above, the navigation array or localizer 52 can be used as the RFID reader 104 or an RFID reader 104 can be integrated therewith to insure that when an instrument or implant moves into the navigation field, it can be compared relative to the plan to insure that the appropriate instrument or implant is being provided at an appropriate time according to the plan.

The reading of the tag of the particular instrument or implant in block 186 can be performed at any appropriate time and according to any appropriate process. For example, when a tag comes within the field of influence of the RFID reader 104, the RFID reader 104 can automatically obtain information from the RFID tag 102. Therefore, the obtaining or reading of the information by the RFID reader 104 in block 186 can be done substantially automatically. In addition, various inputs can be provided to provide instructions or prompts to the RFID reader 104 to obtain the information from the RFID tag. For example, a user can activate the RFID reader 104, according to various embodiments, to obtain information from the RFID tag. Alternatively, or in addition, a switch or portion can be interconnected with a portion of the instrument, such as the handle 122, to provide an instruction to the RFID reader 104 to obtain information from the RFID tag. Therefore, obtaining information from the RFID tag can occur at any appropriate time and can be done substantially automatically or with an input, which can be from a user or other portion of the system.

As discussed above, the information can be obtained from the RFID tag 102 in any appropriate manner, such as automatically, with user input, or a combination thereof. For example, the information from the RFID tag 102 can be read by the RFID reader 104 when positioned relative to the array 52, substantially automatically. Therefore, the user 121 can be alleviated from a responsibility of inputting the appropriate information into the navigation system 20 using various inputs, such as the user input 44. For example, the user 121 maybe required to input a part number, calibration information, size information, identifying information, select an icon, or the like if an automatic system is not provided. Nevertheless, an automatic system can substantially eliminate the need of the user 121 to select or input the appropriate information. Further, the RFID reader 104 can read selected information based upon an input of the user, which can alleviate the user from inputting the detailed information and only requiring that the user to indicate to the navigation system 20 that the RFID reader 104 should read a particular RFID tag 102. Therefore, it will be understood that the RFID reader 104 can read information from the RFID tag to alleviate the user 121 from various tasks, such as inputting information relating to the instrument 24. Further, particular information can be stored in the memory 46, such as calibration information, size information, orientation information, and the like and the RFID tag 102 can simply identify the instrument through the RFID reader 104 for the workstation 42 and the workstation can recall the particular information. Alternatively, the RFID tag 102 can include all of the information required for performing or creating an appropriate icon for display on the display 22 that can be read with the RFID reader 104.

A determination block 188 can be provided to insure that the appropriate instrument or implant is being provided according to the plan formed in block 166. If the determination is NO in block 190 a different instrument or implant can be assembled in block 184 and the information can be read from the new instrument and compared as discussed above. The instrumentation and implant assembly can also be done with confidence according to the present teachings to insure that the procedure is being performed according to the plan 166. Although it will be understood by one skilled in the art that a plan can be altered intraoperatively, the procedure 160 can be provided to insure that if a deviation is made that it is specifically selected by a user, such as the surgeon 121, for the patient 28. Therefore, if the determination is YES in block 192, the instrument or implant that is read can be navigated in block 194.

The navigation in block 194 can proceed according to any appropriate manner, such as those discussed above or understood by one skilled in the art. For example, an icon can be displayed on the display 22 relative to the image data 23 to illustrate the position of the instrument 24 relative to the image data 23. Further, because of the specific information provided from the RFID tag read in block 186, the display can provide a specific illustration of the instrument or implant being navigated in block 194. As the information changes, the work station 42 can provide an appropriate icon on the display 22 to substantially match or mimic the particular implant or instrument being navigated in block 194. Therefore, the procedure 160 can not only confirm that a particular plan is being performed, but can also provide a specific illustration on the display 22 relative to the particular implant or instrument being provided or used. The display of the navigation in block 196 can include the appropriate illustration and the trajectory of an instrument or implant.

Finally, in block 198 the procedure can be completed or performed. The completion of the procedure can include implanting an implant, performing a resection, an ablation, or the like. Nevertheless, the procedure can be performed according to the plan formed in block 166 and navigated with the appropriate navigation system 20. Further, the provision of the particular information can be used to insure that the plan in block 166 has been done with only a selected or particular deviation from the plan inputted in block 166, if desired, or with a particular display on the display 22.

Although one skilled in the art will understand that any appropriate information can be displayed on the display 22 or can be provided in the RFID tag 102, the above-described system is merely exemplary and provided as an example of a selected procedure and instrumentation. For example, as discussed above, new information can be provided onto the RFID tag 102 to be read with the RFID reader 104, which can also be illustrated on the display 22. Further, additional information on the display 22 can include displaying when a particular instrument may be replaced, recalibrated, altered, or the like.

As discussed above, with reference to the flow chart 160 illustrated in FIG. 5, the information provided from the RFID tag 102, according to various embodiments, can be used to display on the display 22 particular information. For example, navigation in block 194 can include illustrating a selected icon on the display 22. With reference to FIGS. 6A and 6B a particular instrument, such as a working portion thereof, can be displayed on the display 22 for navigation.

For example, with reference to FIG. 6A, the probe 124 can be interconnected with the handle 122. The RFID reader 104 positioned near the operating theater and near the probe 124 so that it can read the information from the RFID tag 132, such as in block 170. The information can be transferred along communication line 110 as described in block 187. The information transferred in block 187 can include any appropriate information such as an identification of the probe 124, calibration of the probe 124, or any other appropriate information. The information transferred from the RFID tag 132 to the work station 42 can be used to form an icon 124*i* (e.g. the information can include a rendering or calibration information of the probe 124) of the probe 124 on the display 22. It will be understood that the icon 124*i* can be displayed relative to image data of the patient 28. However, the identification of the probe 124 can be used to display an appropriate size, configuration, geometry, and the like. Therefore, the display 22 can substantially match the configuration of the probe 124. Further, various calibration information from the RFID tag 132 can be used to ensure that the position of various portions of the probe 124 are illustrated appropriated on the display 22.

With reference to FIG. 6B, a different one of the working portion 123 can be interconnected with the handle 122. For example, the tap 128 can be interconnected with the handle 122 that includes the RFID tag 136. The RFID tag 136 can be read by the RFID reader 104 and the information can be transferred along the communication line 110 to the work station 42. Due to the information from the RFID tag 136 read by the RFID reader 104 the display 22 can change the icon to an icon of the tap 128*i*. Not only can the icon change to the tap icon 128*i*, the information from the RFID tag 136 can be used to ensure that appropriate configuration, size, geometry, and the like are illustrated on the display 22.

With continued reference to FIG. 6A-FIG. 6B, and according to various embodiments, the determination of an appropriate icon for display on the display 22 can include various pieces of information. For example, a specific location of the tip of the instrument 24 relative to a portion of the patient 28 for display on the image data 23 can be determined based upon the various calibration and other specific information stored and read from the RFID tag 102. Thus, the display 22 can display the appropriate location of the instrument 24 by displaying an icon based upon the calibration information. This can assist in determining a position of the tip of the instrument 24 relative to a selected of the patient 28 for applying a therapy, minimizing contact with the portion of the anatomy, or other appropriate purposes. Further, as discussed above, the reading of the RFID tag 102 by the RFID reader 104 can be substantially automatic, performed with user input, or any appropriate combination thereof.

Therefore, the flow chart 160 can be used to assist the surgeon 121 in various tasks such as ensuring that the appropriate instrumentation is provided to the operating theater, a particular plan can be performed with the instruments and implants provided, or an illustration of the appropriate icon is on the display 22. As discussed above, as the working portion is interchanged with the handle 122, the display 22 can display an appropriate icon, such as the probe icon 124*i* or the tap icon 128*i*. This allows the display 22 to display the appropriate instrumentation for navigation relative to the patient 28. It will be further understood that the RFID reader 104 can be positioned and substantially automatically read the RFID tags 102 on the various portions of the instrument so that the display 22 can illustrate the appropriate instrument substantially automatically. Further, various mechanisms can be provided to ensure that the display 22 is updated at an appropriate time, such as when the tap 128 is exchanged for the probe 124 with the handle 122. Various mechanisms can be provided such as a foot switch, a touch screen, a connection to the handle 122, or the like to provide a signal to the work station 42 that a change has occurred. Also, the RFID reader 104 alone can substantially automatically read the appropriate RFID tag 132, 136 and sense the difference in the RFID tags and change or transmit the information to the work station 42 to change the display 22. Therefore, the RFID reader 104 can allow for a substantially automatic change of the display 22 without user input due to the substantially active nature of obtaining the data from the RFID tags.

What is claimed is:

1. A system to determine information related to a selected device used with a surgical navigation system for navigating a procedure relative to an anatomy, the system comprising:
   an information tag having a memory operable to store, receive, or transmit a selected information;
   an information tag reader configured to read the selected information from the memory of the information tag, write the selected information to the memory of the information tag, or combinations thereof at least during an operative procedure;
   a surgical instrument associated with the information tag wherein the information tag includes the selected information specific to the surgical instrument;
   a navigation system;
   a communication system interconnecting the information tag reader and the navigation system wherein the selected information read from the information tag is transmitted to the navigation system;
   wherein the information tag reader is further configured to write the selected information to the memory of the information tag during or after a use of the surgical instrument including a change from a previous calibration information including size of the surgical instrument, tip location of the surgical instrument, or orientation of the surgical instrument; and
   a display operable to display a representation of the surgical instrument based upon the information read by the information tag reader from the memory of the information tag including the change in calibration information when previously written, wherein the selected information read by the information tag reader from the memory is read during the operative procedure to ensure that the representation of the surgical instrument is correct.

2. The system of claim 1, wherein the memory of the information tag includes a flash memory storage system interconnected with at least one of a transmission system, a receiving system, or combinations thereof.

3. The system of claim 2, wherein the information tag reader is operable to receive data transmitted from the information tag.

4. The system of claim 2, wherein the information tag reader includes a radio frequency transceiver operable to receive data from the information tag.

5. The system of claim 1, wherein the surgical instrument includes a first portion and a plurality of a second portion;

wherein each of the plurality of second portions are operable to be interconnected with the first portion at a selected time.

6. The system of claim 5, wherein the information tag reader system is operable to automatically obtain information from the information tag via the information tag reader and transmit the information via the communication system to the navigation system.

7. The system of claim 6, wherein at least one of the information tag reader or the navigation system is configured to compare the read selected information to a pre-operative surgical plan and determine that at least the surgical instrument is appropriate for a selected portion of the pre-operative surgical plan.

8. The system of claim 1, wherein the navigation system includes:
a tracking device associated with the surgical instrument;
a localizer configured to track a location of the tracking device;
wherein a position of the surgical instrument is tracked with the tracking device and the position of the surgical instrument is displayed as the representation based on the tracked location of the tracking device and a calibration information or the change in calibration information.

9. The system of claim 8, wherein the localizer includes electromagnetic coils configured to send and receive electromagnetic field and configured to operate as both the information tag reader and to track the location of the tracking device by transmitting and/or receiving electromagnetic fields from both the information tag and the tracking device.

10. The system of claim 1, further comprising:
an imaging device operable to obtain image data of the anatomy;
wherein the image data of the anatomy can be displayed on the display with the information read from the information tag.

11. The system of claim 1, wherein the selected information is information specific to the surgical instrument including information relating to manufacturing of the surgical instrument, information relating to a calibration of the surgical instrument at the time of manufacturing, information regarding calibration of the instrument at a time after manufacturing, information regarding size of the surgical instrument, or combinations thereof.

12. The system of claim 1, wherein the surgical instrument includes at least one of an awl, a drill bit, a screw, a prosthesis, a tap, a probe, or combinations thereof.

13. A system to determine information related to a selected device used with a surgical navigation system for navigating a procedure relative to an anatomy, the system comprising:
an information tag having a member, wherein the information tag is operable to receive and transmit a selected information;
an information tag reader operable to read the selected information transmitted from the information tag, write the selected information to the information tag, or combinations thereof;
a surgical instrument connected to the information tag, wherein the selected information identifies the surgical instrument;
a navigation system having a display device configured to display an icon representing the surgical instrument based on the selected information;
a communication system interconnecting the information tag reader and the navigation system wherein the selected information read from the information tag is transmitted to the navigation system; and
a navigation system processor included with the navigation system configured to compare the selected information that identifies the instrument read from the information tag that is transmitted to the navigation system and a pre-operative surgical plan accessed by the navigation system processor to determine whether the surgical instrument is appropriate as within the pre-operative surgical plan and that the icon represents the surgical instrument connected to the information tag for display with the display device based at least on the selected information read from the information tag;
wherein the pre-operative surgical plan includes surgical plan portions determined and saved prior to an operative procedure including the surgical instrument determined appropriate for at least one surgical plan portion;
wherein the navigation system is configured to provide a signal to a user based on the comparison by the navigation system processor;
wherein the information tag reader is further configured to write the selected information to the memory of the information tag during or after a use of the surgical instrument including a change from a previous calibration information including size of the surgical instrument, tip location of the surgical instrument, or orientation of the surgical instrument.

14. The system of claim 13, wherein the information tag reader is configured to automatically at least one of read the selected information from the information tag, write the selected information to the information tag, or combinations thereof;
wherein the navigation system is configured to automatically provide the signal by the navigation system processor;
wherein the signal is displayed with the display device.

15. The system of claim 14, wherein the information tag reader includes a radio frequency transceiver operable to receive data from the information tag;
wherein the information tag is a radio frequency identification tag that includes a memory storage portion.

16. The system of claim 14,
wherein the surgical instrument includes a plurality of surgical instruments;
wherein the information tag includes a plurality of information tags;
wherein each surgical instrument of the plurality of surgical instruments includes at least one information tag of the plurality of information tags including the selected information relating to the surgical instrument that includes the at least one information tag;
wherein the information tag reader is operable to at least one of read the selected information from the information tag, write the selected information to the information tag, or combinations thereof prior to navigating the procedure to confirm that at least a selected plurality of the plurality of surgical instruments are in the pre-operative surgical plan;
wherein the plurality of surgical instruments includes at least one surgical instrument to perform a portion of the operative procedure or at least one implant to be implanted during the operative procedure.

17. A system to determine information related to a selected device used with a surgical navigation system for navigating a procedure relative to an anatomy, the system comprising:
- a navigation system having a localizer, a processor, and a memory system;
- an information tag member having a memory operable to receive and transmit a selected information;
- an information tag reader incorporated into the localizer, wherein the information tag reader is configured to at least one of read the selected information from the memory of the information tag member, write the selected information to the memory of the information tag member, or combinations thereof;
- a surgical item including the information tag member, wherein the selected information includes information specific to the surgical item;
- a communication system interconnecting the information tag reader and the navigation system wherein the selected information read from the memory of the information tag member is transmitted to the navigation system; and
- a display operable to display information regarding the surgical item based upon the selected information read by the information tag reader from the memory of the information tag member;
- wherein the navigation system is configured to determine a representation of the surgical item to be displayed with the display based at least on the read selected information;
- wherein the memory system stores a surgical plan configured to be recalled by the processor, wherein the surgical plan includes at least a particular surgical item to be used during a surgical procedure;
- wherein the processor is configured to compare the read selected information to the surgical plan recalled from the memory system and determine that at least the surgical item is appropriate for the planned procedure when compared to the particular surgical item;
- wherein the information tag reader is further configured to write the selected information to the memory of the information tag during or after a use of the surgical instrument including a change from a previous calibration information including size of the surgical instrument, tip location of the surgical instrument, or orientation of the surgical instrument.

18. The system of claim 17, wherein the localizer includes electromagnetic coils configured to read the selected information or write the selected information from the member of the information tag member.

19. The system of claim 17, wherein the information tag reader is configured to automatically read the memory;
- wherein the surgical plan includes surgical plan portions determined before the surgical procedure;
- wherein the selected information automatically read from the memory is compared to the surgical plan to confirm that the surgical item including the information tag member is planned for a selected surgical plan portion of the surgical plan portions.

20. The system of claim 19, further comprising:
- a tracking device connected relative to the surgical item; and
- a tracking system configured to track a location of the tracking device;
- wherein the surgical item includes at least one of a surgical instrument or a surgical implant;
- wherein the representation of the surgical item to be displayed with the display is based on both the tracked location and the read selected information.

* * * * *